United States Patent
Rittner et al.

(10) Patent No.: US 9,327,146 B2
(45) Date of Patent: May 3, 2016

(54) CABIN SERVICE ARRANGEMENT, FUSELAGE OF AN AIRCRAFT, A METHOD OF EFFECTING A CABIN ATTENDANT CALL

(71) Applicant: INTERTECHNIQUE, Plaisir Cedex (FR)

(72) Inventors: Wolfgang Rittner, Ahrensbok (DE); Marco Hollm, Rosdorf (DE)

(73) Assignee: Zodiac Aerotechnics, Plaisir (FR)

( * ) Notice: Subject to any disclaimer, the term of this patent is extended or adjusted under 35 U.S.C. 154(b) by 273 days.

(21) Appl. No.: 13/896,704

(22) Filed: May 17, 2013

(65) Prior Publication Data
US 2014/0002279 A1   Jan. 2, 2014

Related U.S. Application Data

(60) Provisional application No. 61/665,486, filed on Jun. 28, 2012.

(51) Int. Cl.
*G08B 5/22* (2006.01)
*A62B 7/08* (2006.01)
(Continued)

(52) U.S. Cl.
CPC .............. *A62B 7/08* (2013.01); *A61M 16/20* (2013.01); *A62B 7/00* (2013.01); *A62B 7/02* (2013.01);
(Continued)

(58) Field of Classification Search
CPC .............. B64D 11/00; B64D 11/0007; B64D 11/0015; H05B 37/029; G08B 5/00; G08B 25/001; G08B 25/003; G08B 25/009
USPC ........ 244/118.5; 340/7.1–7.63, 971; 362/471; 725/77
See application file for complete search history.

(56) References Cited

U.S. PATENT DOCUMENTS

| 4,471,353 A | 9/1984 | Cernik |
| 6,528,954 B1 * | 3/2003 | Lys et al. .................. 315/291 |

(Continued)

FOREIGN PATENT DOCUMENTS

| DE | 19502658 C1 | 3/1996 |
| GB | 2285517 | 7/1995 |
| WO | 2011082998 A1 | 7/2011 |

OTHER PUBLICATIONS

European Patent Application No. 13168355.9, Search Report dated Nov. 27, 2015.

*Primary Examiner* — Steven Lim
*Assistant Examiner* — Benyam Haile
(74) *Attorney, Agent, or Firm* — Kilpatrick Townsend & Stockton LLP; Dean W. Russell; Renae Bailey Wainwright

(57) ABSTRACT

This invention relates to cabin service arrangement assigned to at least one passenger seat in a seat row of an aircraft, comprising:
a lighting unit for providing a light projection and at least one man machine interface for operating the lighting unit, wherein
the at least one man machine interface is associated with
an initiating unit for providing an activation of the lighting unit and
a deactivation unit for receiving an indication for deactivation of the light projection, wherein the deactivation is initializable by an external signal, and wherein
the light projection from the lighting unit comprises an illumination, the illumination being adapted to effect a cabin attendant call. According to the invention
the illumination is adapted to be projected to a projection spot outside of the seat row, and
the deactivation of the illumination is effectable from outside of the seat row.

15 Claims, 5 Drawing Sheets

Figure 1:
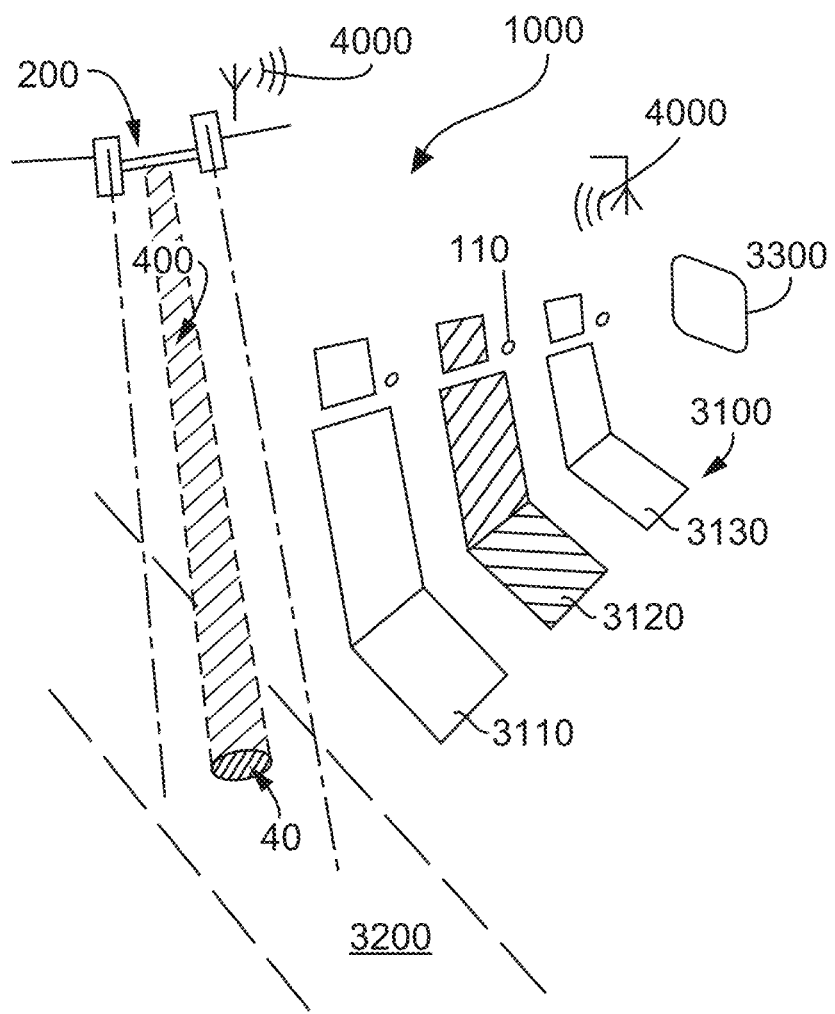

(51) Int. Cl.
*A61M 16/20* (2006.01)
*A62B 7/00* (2006.01)
*B64D 11/00* (2006.01)
*A62B 7/02* (2006.01)
*A62B 7/14* (2006.01)
*A62B 21/00* (2006.01)
*A62B 9/02* (2006.01)
*A62B 18/02* (2006.01)
*B64D 10/00* (2006.01)
*G08B 5/00* (2006.01)
*G08B 5/36* (2006.01)

(52) U.S. Cl.
CPC ... *A62B 7/14* (2013.01); *A62B 9/02* (2013.01); *A62B 18/02* (2013.01); *A62B 21/00* (2013.01); *B64D 10/00* (2013.01); *B64D 11/0015* (2013.01); *B64D 11/00155* (2014.12); *B64D 2231/00* (2013.01); *B64D 2231/02* (2013.01); *G08B 5/00* (2013.01); *G08B 5/224* (2013.01); *G08B 5/36* (2013.01)

(56) References Cited

U.S. PATENT DOCUMENTS

| | | | |
|---|---|---|---|
| 2001/0023499 A1 | 9/2001 | Wakahara | |
| 2005/0002198 A1* | 1/2005 | Blechschmidt | 362/470 |
| 2005/0110952 A1 | 5/2005 | Pho et al. | |
| 2007/0061847 A1* | 3/2007 | Callahan et al. | 725/76 |
| 2009/0112407 A1* | 4/2009 | Kneller | B64D 11/0624 701/45 |
| 2010/0201951 A1 | 8/2010 | Budinger et al. | |
| 2014/0192268 A1* | 7/2014 | Petrisor | G06F 3/0488 348/734 |

* cited by examiner

CABIN SERVICE ARRANGEMENT, FUSELAGE OF AN AIRCRAFT, A METHOD OF EFFECTING A CABIN ATTENDANT CALL

CROSS-REFERENCE TO RELATED APPLICATION

This application claims priority to U.S. Provisional Patent Application No. 61/665,486 filed on Jun. 28, 2012, the contents of which are incorporated herein by reference.

This invention relates to a cabin service arrangement assigned to at least one passenger seat in a seat row of an aircraft according to the preamble part of claim 1. Further this invention relates to a fuselage of an aircraft comprising a cabin service arrangement wherein a light projection provides a cabin attendant call and a method of effecting a cabin attendant call.

In commercial aircrafts the cabin is a section of an aircraft wherein travel class sections can be provided. Beyond that the seats of the passengers are normally arranged in rows and alleys wherein a row usually is aligned crosswise to an alley of seats; a row may have two, three, four, five or more seats depending on the size and the sections of an aircraft.

Cabin service systems are used to provide a number of services. The service can also use a passenger service unit which is widely used in aircrafts. A passenger service unit (PSU) offers comfort, control or safety modules comprising generally a reading light, an attendant call light, a passenger air supply device, oxygen masks, warning lights and the like applications. In some aircrafts a passenger unit is provided for each seat of a passenger and crew member; but providing of the service to a number of seats or rows together is also possible. The arrangement of a PSU is normally above a group of seats beneath the overhead panel and very close to each passenger's seat.

DE 19502658 C1 discloses an arrangement for supplying passengers in a passenger cabin wherein the supply unit is arranged on a flexible, resilient support arm such that the control and comfort elements of the supply unit may be accessed comfortably within the reach of the passenger itself at any time.

In WO 2011/082998 A1 an arrangement of a supply module is described, wherein different passenger seat positions may be illuminated without mechanical positioning or manual adjustment of a supply unit. The supply module is being arranged to offer illumination and different services or functions like visual information, acoustic information, air control surfaces or medical oxygen next to the passenger. The activation of the supply module is effected by a control unit wherein the operating bases on a pre-definable seating configuration of the passenger.

In U.S. 2007/006187 A1 a cabin service system is disclosed comprising a wireless network and a communication system for controlling the cabin service supported by a cabin attendant panel for minimizing the amount of required wiring combined with an easy to use passenger service system which is ergonomically designed for its passenger.

Still, these kinds of cabin service arrangements with a passenger service unit have drawbacks as to the handling comfort and implementation in an aircrafts cabin. It is desirable to improve comfort for the passenger but nevertheless appreciating an improved technical realization of the passenger service unit and the technical implementation into the cabin of an aircraft.

This is where the invention comes in, a major object of the invention is to provide a cabin service arrangement assigned to at least one passenger in a seat row, a fuselage of an aircraft and a method of operating a cabin service arrangement, in particular in cooperation with a passenger service unit, which is adapted for a technically improved supply of a cabin attendant call with increased comfort for the passenger and also the flight attendant. In particular the cabin service arrangement has a related apparatus which is part of a passenger service unit. It is still a further objet of this invention to adjust the activation and/or deactivation of the aforementioned passenger attendant call function in an improved way.

In relation to the cabin service arrangement the object of this invention is achieved by the cabin service arrangement as mentioned in the introduction and according to the invention further providing the features of the characterizing part of claim 1. Thus, the invention relates to a cabin service arrangement assigned for at least one passenger seat in a seat row of an aircraft, comprising:
a lighting unit for providing a light projection and at least one man machine interface for operating the lighting unit, wherein
the at least one man machine interface is associated with
  an initiating unit for providing an activation of the lighting unit and
  a deactivation unit for receiving an indication for deactivation of the light projection,
  wherein the deactivation is initialisable by an external signal, and wherein
the light projection from the lighting unit comprises an illumination, the illumination being adapted to effect a cabin attendant call.

According to the invention
the illumination is adapted to be projected to a projection spot outside of the seat row, and
the deactivation of the illumination is effectable from outside of the seat row.

The invention also leads to a fuselage of an aircraft comprising a number of passenger service units and associated therewith a number of cabin service arrangements, in particular wherein the cabin service arrangement is partly or in total integrated in an associated passenger service unit.

In relation to the method the object is achieved by a method of effecting a cabin attendant call by operating a cabin service arrangement assigned to at least one passenger seat in a seat row of an aircraft, comprising a lighting unit for providing a light projection and at least one man machine interface for operating the lighting unit, wherein
the at least one man machine interface is associated with
  an initiating unit for providing an activation of the lighting unit and
  a deactivation unit for receiving an indication for deactivation of the light projection,
  wherein the deactivation can be initiated by an external signal, and wherein
the light projection from the lighting unit comprises an illumination, the illumination being adapted to effect the cabin attendant call. According to the invention the method comprises the steps of:
the illumination is projected to a projection spot outside of the seat row, and
the deactivation of the illumination is effected from outside of the seat row.

Thus basically, this invention provides an apparatus and a method based on a cabin service arrangement wherein the illumination of the cabin attendant call is placed outside of the seat row and its deactivation is also executable from the outside of the seat row.

In relation to the apparatus a particular preferred development leads to a communication between the aforementioned units and further units; in particular a control unit of dependent claim 5 and an external unit of dependent claim 10 and/or 11.

The invention recognized that it is desirable to activate a cabin attendant call comfortable for the passenger and clearly visible for the flight attendant. Thus, this invention provides an inventive concept of a light projection of an attendant call light wherein the light projection is adapted by an illumination. The illumination of this invention is projected to a projection spot outside of the seat row while the activation; preferably by pressing a call button close to the overhead panel or an arm rest, in particular in a passenger service unit or a passenger service unit system respectively.

The projection outside of the seat row according to the invention, preferably in the gangway e.g., in addition combines some different further improved aspects of comfort and reliability. Projecting the light outside of the seat row, e.g. in the gangway or on the floor, increases the visibility of a signal light for the flight attendant. Further, the illumination of the passengers or the passenger's seat remains in their light projection without changing light settings. This increases the comfort of the passengers because in the prior art the signal light was directed on the passenger by changing the light settings into a visible attendant call light. According to the concept, shifting of the signal lights illumination to a projection spot located outside of a seat row leads to a faster response of the flight attendant. Also the reliability of the flight attendant increases because of the better overview over an illumination pattern; namely a passengers reading light and the illumination on the projection spot meant to effect a cabin attend call are separated. This significantly improves availability and identification of the cabin attend call.

According to this invention an initiating unit is provided for activation of the lighting unit, which is providing a light projection for illuminating on a projection spot outside of the seat row. In a preferred development this lighting unit can be placed close to the reading light in the overhead panel, integrated in the reading light or elsewhere in the passenger service unit. Also, additionally or alternatively, a lighting unit can be placed separately outside of the seat row; the illumination in both cases should be projected outside of the seat row and can be placed on varied surfaces.

The lighting unit will be able to adjust the illumination of a cabin attendant call in each position or projection spot. An easy handling for activating the flight attendant call is known in the state of art, but the attendant call light itself, usually integrated in the reading light device, is typically directed towards to the passenger's seat. The visibility of an illumination for a flight attendant is much higher when the illumination is projected to or in the gangway. The flight attendant obtains a good view of gangway and therefore also of the illumination. This enables a promptly reaction on the cabin attendant call. The assignment of the call to the single passenger can be regulated by the projection spot but definitely the illumination itself. The illumination is not regulated anymore by the possibilities of the reading light and can be changed to new light signals because of the independency of passenger's seat. The reading light, which is directed on a passenger's seat, should not or less disturb the passenger itself. The change of the projection spot offers new possibilities for the attendant call light, increases the comfort zone and provides a higher reliability of the passenger's assignment.

The invention also recognized that is desirable to adapt a deactivation of the cabin attendant call just as the projection uncoupled of the passenger's seat and seat rows after the arrival of the flight attendant to the passenger. The invention provides a deactivation of the illumination outside of the seat row which is also effectable from the outside of the seat row without using the initiating unit. This is of advantage as the initiating unit like an attendant call button, switches and so on usually are close to the passenger seat and a passenger thus could adversely be effected by a movement of the attendant when deactivating the illumination. In the prior art the flight attendant has to cancel the cabin attend call at the call button, which means pressing the button in the seat row independent of the seat position and its reach ability. A row with three seats thus can become a very uncomfortable dislocation of the arm of the flight attendant also for the passenger. According to this invention a deactivation unit receives an indication for deactivation of the light projection, wherein the deactivation is initiated by an external signal. The handling of deactivation is significantly improved for the involved flight attendant because of external signal—outside of the seat rows. This increases the comfort and free space for the passenger and but also for the surrounding passengers.

It is to be understood that a cabin attendant call is not limited to a call signal itself but beyond or alternatively to a call signal itself can comprise any kind of information item, indication of order, urging wish, emergency situation indication or the like attendant call item which is emitted from the passenger; be that it may be a communication item which demands for a reaction and interaction of the flight attendant (like an order of a meal e.g.) or be that it may be just an information item without a necessity to communicate (like a demand of not being disturbed or the information of the kind of meal which has been ordered by a passenger on a certain seat).

These and further developed configurations are further outlined in dependent claims. Thereby, the mentioned advantages of the proposed concept are even more improved. For each feature of the dependent claims it is claimed independent protection independent from all other features of this disclosure.

In a particular preferred development it has been recognized to be a convenience when the illumination is projected to the outside of the seat row's occupation area and also the deactivation of the illumination is effectable from outside of the seat row's occupation area. Whereas the seat row is meant to be the body of the seat row itself a seat row's occupation area is meant to be basically at least the volume in an edge frame for a designed installation space of the seat row plus passengers. Preferably a seat row's occupation area in a particular preferred development is meant to be an area well exceeding the aforementioned volume such that a seat row's occupation area only comprises an area in sight of a passengers view when sitting in more or less forward direction in his seat. In other words, a location outside of the seat row's occupation area is meant to be a space not directly visible by the passenger when sitting in a more or less forward direction in his seat but still visible, preferably well visible, by a flight attendant.

The illumination of a cabin attendant call can change the lightness of the passenger zone. By providing an illumination outside of the seat row's occupation area the annoying of the passengers decreases and the visibility of the flight attendant increases staying typically outside of the seat row's occupation area. It so does not matter if passengers are in the gangway and decrease the field of vision for the flight attendant. The illumination indicates the cabin attend call and offers a clearly visibly assignment and therefore the realizing and the reacting of the flight attendant are improved.

In a particular preferred development the deactivation unit has a sensor unit. This feature is beneficiate to generate an incoming signal detected by a sensor unit to generate an deactivation signal. Preferably the sensor unit is adapted to receive a touch free user input to the man machine interface. A preferred sensor unit detects changes of e.g. lighting or temperature conditions and therefore input motions can be used for deactivation like a whipping of a hand. This offers the possibility for the flight attendant to deactivate very easily and quickly without the necessity of a special button or device outside of the seat row. A sensor unit can be placed in the gangway combined with the lightening unit or divided in different units. This increases the flexibility of the cabin service arrangement and the integration in the supply modules of the aircraft.

In a particular preferred development the information of the seat for providing an illumination of a cabin attend call outside of the seat row is stored by a control unit and/or in an initiating unit assigned to at least one seat. Stored information enables the precise assignment of the cabin attendant call. Additionally there is an increasing of comfort of the passenger and knowledge of the flight attendant because the stored information offers the opportunity to interact with the passenger's need which increases the feeling of being adequately supplied. The combination of the stored location, both in a control unit and initiating unit, provides a very flexible system of a cabin service arrangement.

In a particular preferred development the illumination provides stored information of the passenger seat to the place outside of the seat row; preferably wherein the illumination comprises light signs, highlighter, light pattern and so on. Particular preferred is that the illumination comprises one or more lighting effects selected from the group consisting of: a light sign, a highlighter, a light pattern, in particular, flashing, varying in color, intensity and/or place of spot as a function of time. This development offers an advantaged cabin attendant call because of the providing of additional information beside the location of the calling passenger seat. Further more this kind of illumination offers information also in form of color sequences, light signs, words or light pattern which will be placed outside of the seat row therefore visible for the flight attendant. Par examples the form of address can be personified by the cabin attendant call because of an additional illumination of the name of the passenger or his personal information; this also generates a personalized interaction of the flight attendant with the calling passenger.

In a particular preferred development a control unit processes the incoming data of the units and provides operator responses to the units. In the case that the cabin attendant call required operator response, the control unit has the ability for providing calculated data. In the easiest way it is the turn out of the cabin attendant call light, also by an incoming motion. But also the providing of information as from one to the other flight attendant will be processed in the control unit.

Preferably a projection spot is outside of the seat row is located in the volume area between the gangway and the ceiling above the gangway. In a particular preferred development the projection spot is supported by a fixed spot location like e.g. the floor lightning. In commercial airlines the cabin attendant call only consists of a light which is directed towards the passenger's seat. For the quick and easy response of a flight attendant the integration of further illumination or light projection is according to the concept additionally to the illumination outside of the seat row.

Additionally or alternatively the projection spot is outside of the seat row is located on a movable spot location; like e.g. in form of a service platform, in particular a trolley, a tablet or the like service personal item. The overview is increased by a fixed and/or movable lightening such as florescent light and simplifies the guiding of the flight attendant.

In a particular preferred development the illumination outside of the seat rows marks a cabin zone. Flight attendants typically get an area of responsibility during the flight; this can be divided in different zones. The inventive development enlarges the illumination of at least one passenger seat of a seat row up to the cabin zone which signals the relevant authority for the cabin attend call.

In a particular preferred development the illumination outside of the seat row is controllable by an external service unit. The cabin service arrangement is one of the supply units and modules of an aircraft and should have the function of a single device but being controllable externally in certain situation like central position of starting, landing or further situations. The external service unit should be able to provide central orders for the illumination outside of the seat row.

In a particular preferred development the initiating unit activates additionally to the illumination outside of the seat row an external service unit for receiving information about the cabin attend call. The stored information of each passenger's seat for the cabin attendant call should be provided also to the external service unit so that in each situation the stored information can be shared in the aircraft and a higher service is made possible. During catering service it is normally difficult for the flight attend to react. In this case an additional not involved flight attendant can responses to the flight attend call with all information he needs for a satisfying service. The development offers an advantageously degree of freedom for the flight attendant after realizing the illumination of an cabin attend call light outside of the seat rows.

In a particular preferred development the illumination outside of the seat row is deactivated by deactivating of the initiating unit itself. This development enables the passengers itself to deactivate without waiting so for the flight attendant or using the deactivation unit. This deactivation will be registered by the control unit and will be sent to the external unit. This offers the possibility for the flight attendant to get this information and might asked to increase the service and comfort feeling of the passengers.

In a particular preferred development the external service unit is adapted the information of illumination outside of the seat row for other service devices. The inventive development includes the idea of a diversified service thinking integrating different types of devices for the support of the flight attendant. While catering a catering trolley can integrates a pad for getting information of the external service unit of the cabin attendant call which is illuminate outside of the seat rows. Getting the signal the flight attend can recognizes the signal, getting the information, can indicate also the illumination and might interact with other flight attendants for a higher service and faster response for the initiated call.

In a particular preferred development the communication of the units is based on wireless network for providing the illumination outside of the seat. The cabin service arrangement with an external service unit and additionally devices needs a high degree of freedom in the installation for each device for providing an illumination to a projection spot outside of the seat row, especially for the cabin service arrangement with included units. Otherwise the connection between the units and devices are difficult to handle. A wireless connection simplified the practices for installation and offers a higher utilization of the multifunctional designed aircraft.

For a more complete understanding of the invention, the invention will now be described in detail with reference to the accompanying drawing. The detailed description will illustrate and describe what is considered as a preferred embodiment of the invention. It should of course be understood that various modifications and changes in form or detail could readily be made without departing from the spirit of the invention. It is therefore intended that the invention may not be limited to the exact form and detail shown and described herein, nor to anything less than the whole of the invention disclosed herein and as claimed hereinafter. Further the features described in the description, the drawing and the claims disclosing the invention may be essential for the invention considered alone or in combination. In particular, any reference signs in the claims shall not be construed as limiting the scope of the invention. The wording "comprising" does not exclude other elements or steps. The wording "a" or "an" does not exclude a plurality. The wording, "a number of" items, comprises also the number one, i.e. a single item, and further numbers like two, three, four and so forth.

Figure 2:
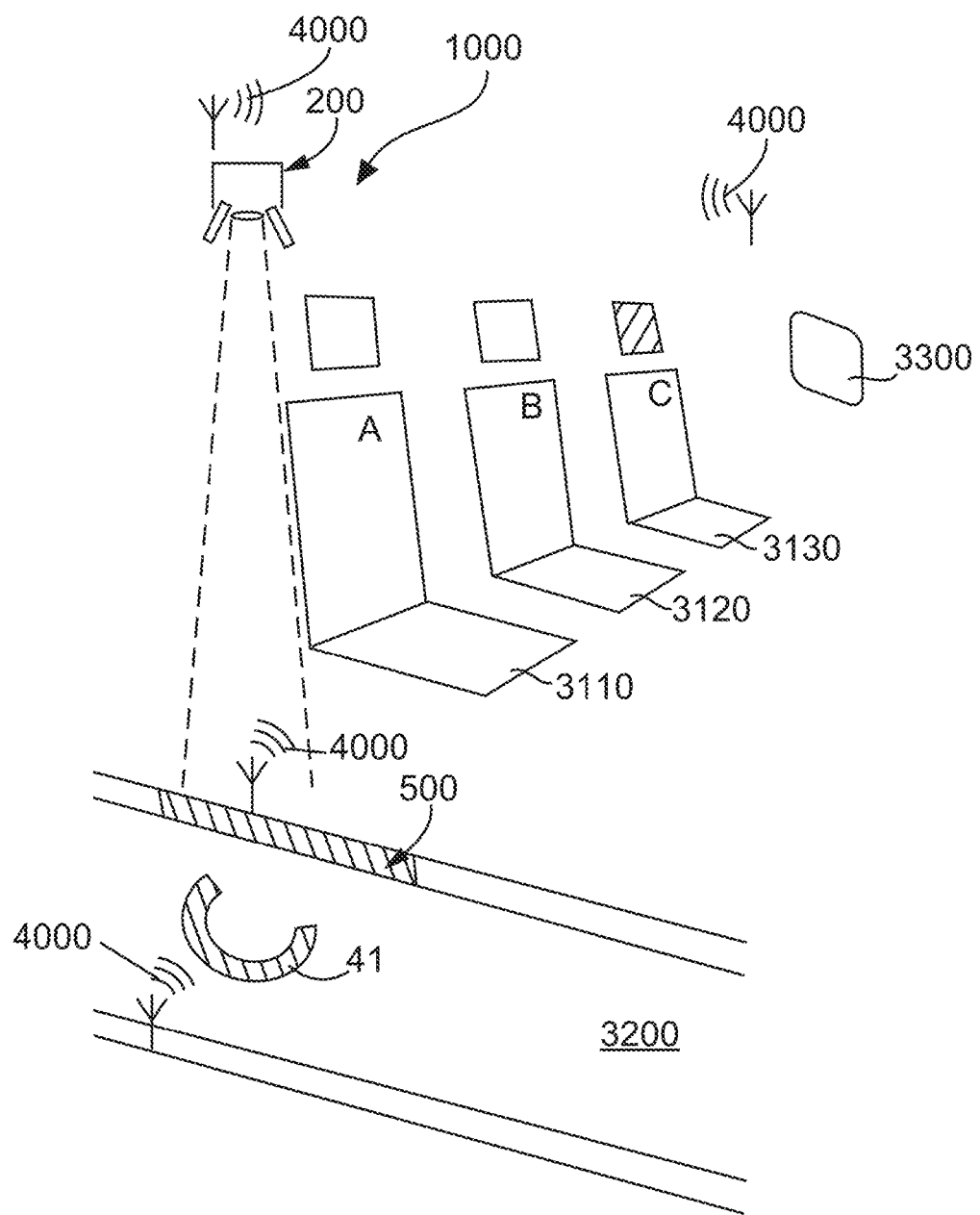
Figure 3:
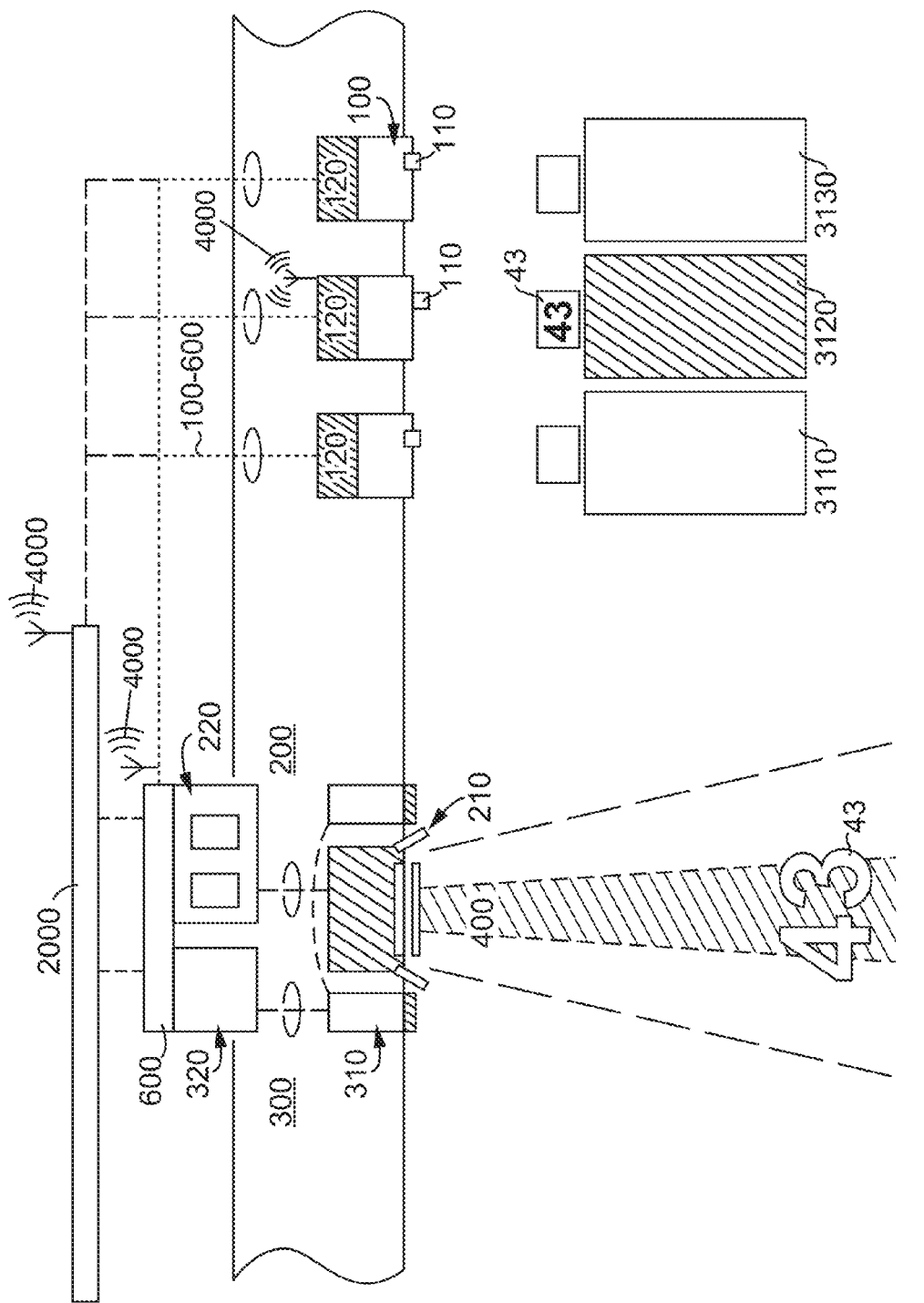
Figure 4:
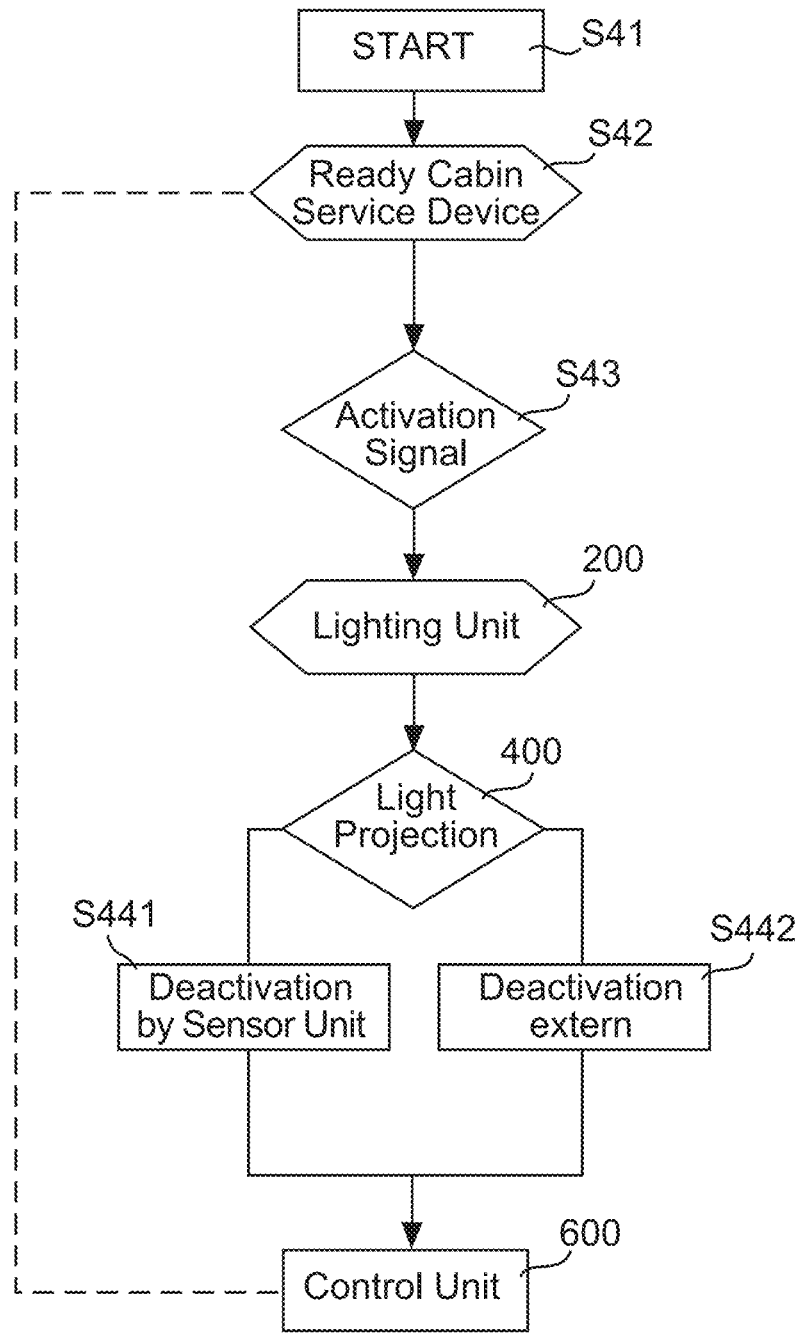
Figure 5:
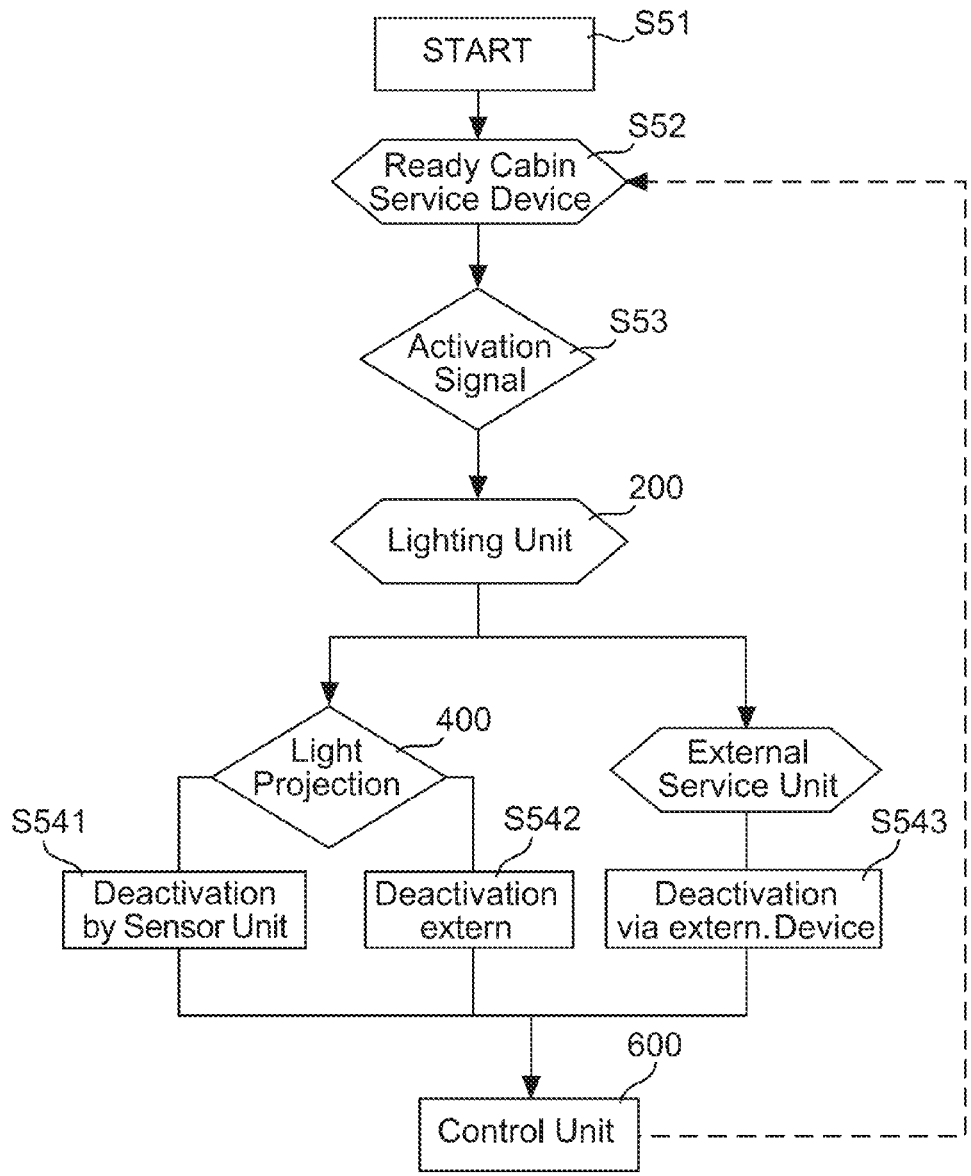

The drawing shows in,

FIG. 1: a first embodiment a simplified scheme of an illumination of a cabin attendant call outside of the seat row for one passenger seat in a seat row of an aircraft arranged in an overhead panel above the gangway;

FIG. 2: a second embodiment a simplified scheme of light projection of an cabin attendant call on the floor of the gangway and in addition a light projection of a light integrated in the floor;

FIG. 3: a third embodiment a light projection in form of an illumination of an cabin attendant call outside of the seat row for one passenger seat in a seat row including a sensor unit;

FIG. 4: a fourth embodiment a simplified flow chart illustrating the operating of light projection of a cabin attendant call outside of the seat row combined with different deactivation steps;

FIG. 5: a fifth embodiment of simplified flow chart illustrating the operating of light projection of a cabin attendant call outside of the seat row combined with different deactivation steps and additional devices.

FIG. 1 shows a cabin service arrangement 1000 with a simplified scheme of an illumination 40 of a cabin attendant call outside of the seat row 3100. At a window 3300, the seat row 3100 includes three passenger's seats 3110, 3120, 3130, wherein one seat 3120 is marked for accentuating the initiated cabin attendant call. The initiating is visible shown by a black dot as a button 110 of the initiating unit 100, the simplified cabin attendant call button. In this case no signal connection is shown so that the radio transmission 4000 transmission is used. After initiating the lighting unit 200, a light projection 400 provides an illumination 40 which signals the flight attendant the attendant call clearly visible as a light pattern or alternate light pattern on the floor of the gangway 3200.

For identical or equivalent items or items of identical or equivalent function in the following the some reference marks are used. For corresponding features thus it is referred to the above description.

FIG. 2 shows a cabin service arrangement 1000 with a simplified scheme of an illumination 41 in form of an alphabetic character with an additional floor lightening 500. The signal connection is effected wireless, in this case by radio transmission 4000. The floor lighting can be a light emitting electrode, such as an OLED for emitting light as a signal for the cabin attendant call light. In combination with the projected alphabetic character the flight attendant can on one hand very easily recognize the call itself without a close look in the seat rows beyond the storage space and on the other hand realize the precise location of the seat. Because of the decentralized system the passenger will not be influence in his comfort position by changed lighting conditions or settings.

FIG. 3 shows a simplified scheme of an illumination 43 in form of a three dimensional number, in this case 43, which is projected in the gangway. The seat 3120 is marked in this FIG. 3 for depicting the seat with the seat number 43 for giving the initiation for the cabin attendant call. The initiating unit 100 provides the activation with a button 110 of the activation unit, including stored information in a section 120 of the initiating unit. In this figure the initiating unit 100 is either signal line connected (dashed line) 100-600 or is effected by wireless, both is possible in this context, and activate the lighting unit 200. The lighting unit provides a light projection adapted by a lighting module 210 and a lighting assembly 220. The instrumental apparatus of the lighting module is variable. The apparatus should integrate beam forming elements and light forming elements. The lighting assembly 220 integrates control and actuation modules for the beam width, beam focus and beam direction and for light color and light temperature. Therefore the light projection can provide an illumination or an illumination pattern which can be clearly identified, whereat the information is stored in the control unit 600. The communication or information transfer of all units and the external service unit 2000 can be adapted wireless. In the figure there are two options to deactivate the light projection: first by a control unit 600 of an external service unit or second by a deactivation unit 300. In FIG. 1 the deactivation unit 300 integrates a sensor unit 310 and a sensor assembly 320. Therefore the connection is a sensing signal line connection. The sensor assembly should integrate infrared sensor modules and stray light modules which are sensing signal connected to the infrared sensor and stray light sensor itself. The sensor unit 310 offers the opportunity for the flight attendant by arriving to the calling passenger to deactivate the cabin attendant call by a motion. The sensor unit 310 detects the signal of the incoming motion and this signal will be processed to a deactivation signal. A button or pad is also possible for receiving a deactivation signal of the deactivation unit 300. In FIG. 1 the deactivation unit 300 is uncoupled of the passenger's seat for providing the highest comfort.

FIG. 4 shows a simplified flow chart illustrating the operating of light projection of a cabin attendant call outside of the seat row 3100 combined with different deactivation steps. After the start S41 of the system of an aircraft the cabin service arrangement is adapted in S42 to the passenger. After the activation signal the initiating unit transmits in S43 the activation signal to the lighting unit 200. The lighting unit 200 will provide a light projection 400 adapted to provide a cabin attendant call which can be deactivated in two ways. One way S441 can be the deactivation by the deactivation unit 300, like a sensor unit 310, the other way S442 can be the deactivation with the external service unit. The control unit 600 at the external service unit will transmit the deactivation and get the cabin service arrangement in the initial position.

FIG. 5 shows a simplified flow chart illustrating the operating of light projection of a cabin attendant call outside of the seat row 3100 combined with different deactivation steps and the activation of an external device. After the start S51 of the system of an aircraft the cabin service arrangement is adapted in S52. After the activation signal the initiating unit transmits in S53 the activation signal to the lighting unit 200. The lighting unit 200 will provide a light projection 400 adapted to provide a cabin attendant call which can be deactivated in two ways. One way S541 can be the deactivation by the deactivation unit 300 like a sensor unit 310; the other way S542 can be the deactivation with the external service unit. The control unit 600 of the external service unit will transmit the deactivation and get the cabin service arrangement in the initial position. It is also possible to deactivate in S543 the cabin attendant call by an external device like a pad next to the catering trolley.

The invention claimed is:

1. A cabin service arrangement assigned to at least one passenger seat in a seat row of an aircraft, comprising:
   a lighting unit for providing a light projection and at least one interface for operating the lighting unit, wherein the at least one interface is associated with:
      an initiating unit for activation of the lighting unit; and
      a deactivation unit for deactivation of the light projection, wherein the deactivation of the light projection is initiated by an external signal, and wherein
   the light projection from the lighting unit comprises an illumination, the illumination being adapted to effect a cabin attendant call,
   and wherein:
      the illumination is adapted to be projected to a projection spot outside of the seat row and outside of an occupation area of the seat row,
      the illumination outside of the seat row and outside of the occupation area of the seat row is controllable by an external service unit,
      the deactivation of the light projection is effectable from outside of the seat row and outside of the occupation area of the seat row, and
      the projection spot is located outside of the seat row and outside of the occupation area of the seat row in a volume area between a gangway and a ceiling above the gangway, wherein the projection spot is located on at least one of a fixed spot location and a movable spot location.

2. The cabin service arrangement according to claim 1 wherein at least one of the initiating unit and the deactivation unit has a sensor unit adapted to receive a touch free user input to the interface.

3. The cabin service arrangement according to claim 1 wherein the illumination provides stored information of the passenger seat to the projection spot outside of the seat row, and wherein the illumination comprises one or more lighting effects selected from the group consisting of: a light sign, a highlighter, and a light pattern, wherein the illumination may vary in at least one of color, intensity and place of spot as a function of time.

4. The cabin service arrangement according to claim 1 wherein a control unit is adapted to process incoming data of at least one of the initiating unit and the deactivation unit and the control unit provides an operator response to at least one of the initiating unit and the deactivation unit.

5. The cabin service arrangement according to claim 1 wherein information of the passenger seat for providing the illumination outside of the seat row and outside of an occupation area of the seat row is stored by at least one of a control unit and an initiating unit assigned to at least one seat.

6. The cabin service arrangement according to claim 1 wherein the projection spot is supported by a fixed spot location in the form of at least one of a floor lighting and a movable spot location in the form of a service platform.

7. The cabin service arrangement according to claim 1 wherein the illumination outside of the seat row and outside of an occupation area of the seat row marks a cabin zone.

8. The cabin service arrangement according to claim 1 wherein the initiating unit is adapted to activate an external service unit for receiving information about the cabin attendant call.

9. The cabin service arrangement according to claim 1 wherein the illumination outside of the seat row and outside of an occupation area of the seat row is deactivatable by of the initiating unit itself.

10. The cabin service arrangement according to claim 8 wherein the external service unit is adapted to handle information of illumination outside of the seat row for other service devices.

11. The cabin service arrangement according to claim 1 wherein communication of at least one of the initiating unit and the deactivation unit is via a wireless network for providing the light projection outside of the seat row and outside of an occupation area of the seat row.

12. The fuselage of an aircraft comprising a number of passenger service units and associated therewith a number of cabin service arrangements according to claim 1, wherein the cabin service arrangement is partly or in total integrated in an associated passenger service unit.

13. A method of effecting a cabin attendant call by operating a cabin service arrangement assigned to at least one passenger seat in a seat row of an aircraft comprising a lighting unit for providing a light projection and at least one interface for operating the lighting unit, wherein
   the at least one interface is associated with:
      an initiating unit for providing an activation of the lighting unit; and
      a deactivation unit for receiving an indication for deactivation of the light projection, wherein the deactivation can be initiated by an external signal, and wherein
   the light projection from the lighting unit comprises an illumination, the illumination being adapted to effect the cabin attendant call,
   wherein:
      the illumination is projected to a projection spot outside of the seat row and outside of an occupation area of the seat row, and the illumination outside of the seat row and outside of the occupation area of the seat row is controllable by an external service unit,
      the deactivation of the light projection is effected from outside of the seat row and outside of the occupation area of the seat row, and
      the projection spot is located in a volume area between a gangway and a ceiling above the gangway, wherein the projection spot is located on at least one of a fixed spot location and a movable spot location.

14. The cabin service arrangement according to claim 6 wherein the service platform is a trolley, a tablet, or a service personal item.

15. A cabin service arrangement assigned to at least one passenger seat in a seat row of an aircraft, comprising:
   a lighting unit for providing a light projection and at least one interface for operating the lighting unit, wherein the at least one interface is associated with:
      an initiating unit for providing an activation of the lighting unit; and
      a deactivation unit for receiving an indication for deactivation of the light projection, wherein the deactivation of the light projection is initiated by an external signal, and wherein the light projection from the lighting unit comprises an illumination, the illumination being adapted to effect a cabin attendant call,
   and wherein:
      the illumination is adapted to be projected to a projection spot outside of the seat row;
      the illumination outside of the seat row and outside of an occupation area of the seat row is controllable by an external service unit;
      the deactivation of the light projection is effectable from outside of the seat row; and
      the projection spot is located in a volume area between a gangway and a ceiling above the gangway, wherein the projection spot is supported by a movable spot location in the form of a service platform.

* * * * *